(12) United States Patent
Banju et al.

(10) Patent No.: US 10,632,427 B2
(45) Date of Patent: Apr. 28, 2020

(54) FILTRATION FILTER

(71) Applicant: Murata Manufacturing Co., Ltd., Nagaokakyo-shi, Kyoto-fu (JP)

(72) Inventors: Masaru Banju, Nagaokakyo (JP); Takashi Kondo, Nagaokakyo (JP); Junko Watanabe, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 223 days.

(21) Appl. No.: 15/719,942

(22) Filed: Sep. 29, 2017

(65) Prior Publication Data
US 2018/0021737 A1      Jan. 25, 2018

Related U.S. Application Data

(63) Continuation of application No. PCT/JP2016/081158, filed on Oct. 20, 2016.

(30) Foreign Application Priority Data

Dec. 14, 2015   (JP) .................. 2015-243476

(51) Int. Cl.
*B01D 71/02*   (2006.01)
*B01D 63/08*   (2006.01)
(Continued)

(52) U.S. Cl.
CPC .......... *B01D 71/022* (2013.01); *B01D 29/01* (2013.01); *B01D 46/0004* (2013.01);
(Continued)

(58) Field of Classification Search
CPC .... B01D 71/022; B01D 69/02; B01D 63/087; B01D 69/10; B01D 2315/10;
(Continued)

(56) References Cited

U.S. PATENT DOCUMENTS 6,221,122 B1   4/2001 Gieseke et al.
6,884,341 B2   4/2005 Ferguson
(Continued)

FOREIGN PATENT DOCUMENTS

DE   102006009623 A1   9/2007
JP     S56-31825 U      3/1981
(Continued)

OTHER PUBLICATIONS

International Search Report issued in International Application No. PCT/JP2016/081158, dated Dec. 13, 2016.
(Continued)

*Primary Examiner* — Lucas A Stelling
*Assistant Examiner* — Angel Olivera
(74) *Attorney, Agent, or Firm* — Arent Fox LLP

(57) ABSTRACT

A filtration filter is suitable for performing cross-flow filtration by using a metallic porous membrane. A metallic porous membrane has a membrane portion for filtering filtration objects contained in a fluid and a held portion provided at its outer periphery. A first frame member and a second frame member hold the held portion of the metallic porous membrane there between. The held portion has a bent portion bent to a second principal surface side opposing a first principal surface of the membrane portion. The first frame member is in contact with the held portion at the first principal surface side of the metallic porous membrane. The second frame member is disposed at an inner side portion of the first frame member and is in contact with the held portion at the second principal surface side of the metallic porous membrane.

20 Claims, 9 Drawing Sheets

(51) Int. Cl.
*B01D 65/00* (2006.01)
*B01D 46/24* (2006.01)
*B01D 29/01* (2006.01)
*B01D 29/05* (2006.01)
*C12M 1/12* (2006.01)
*B01D 69/10* (2006.01)
*B01D 46/00* (2006.01)
*B01D 69/02* (2006.01)
*C12M 1/26* (2006.01)
*C12M 1/00* (2006.01)
*B01D 29/03* (2006.01)

(52) U.S. Cl.
CPC ..... *B01D 46/0005* (2013.01); *B01D 46/2444* (2013.01); *B01D 63/087* (2013.01); *B01D 65/003* (2013.01); *B01D 69/02* (2013.01); *B01D 69/10* (2013.01); *C12M 1/12* (2013.01); *B01D 29/03* (2013.01); *B01D 29/05* (2013.01); *B01D 2313/025* (2013.01); *B01D 2313/20* (2013.01); *B01D 2315/10* (2013.01); *B01D 2315/20* (2013.01); *B01D 2325/04* (2013.01); *C12M 29/18* (2013.01); *C12M 33/14* (2013.01); *C12M 47/02* (2013.01)

(58) Field of Classification Search
CPC .......... B01D 2313/20; B01D 2313/025; B01D 2325/04; B01D 65/003; B01D 29/01; B01D 29/03; B01D 29/05; C12M 1/12; C12M 47/02; C12M 33/14; C12M 29/18
See application file for complete search history.

(56) References Cited

U.S. PATENT DOCUMENTS

| | | |
|---|---|---|
| 2004/0065622 A1 | 4/2004 | Ferguson |
| 2005/0189286 A1 | 9/2005 | Ferguson |
| 2017/0239625 A1 | 8/2017 | Ishikawa et al. |

FOREIGN PATENT DOCUMENTS

| | | |
|---|---|---|
| JP | S59-154322 U | 10/1984 |
| JP | S60-86433 U | 6/1985 |
| JP | S62-123737 U | 8/1987 |
| JP | S63-242303 A | 10/1988 |
| JP | H02-25006 U | 2/1990 |
| JP | 2000-167318 A | 6/2000 |
| JP | 2002-537523 A | 11/2002 |
| JP | 2003-93817 A | 4/2003 |
| JP | 2006-501450 A | 1/2006 |
| JP | 2013-210239 A | 10/2013 |
| WO | WO 2015/151762 A1 | 10/2015 |

OTHER PUBLICATIONS

Written Opinion of the International Searching Authority issued in International Application No. PCT/JP2016/081158, dated Dec. 13, 2016.

FILTRATION FILTER

CROSS REFERENCE TO RELATED APPLICATIONS

The present application is a continuation of International application No. PCT/JP2016/081158, filed Oct. 20, 2016, which claims priority to Japanese Patent Application No. 2015-243476, filed Dec. 14, 2015, the entire contents of each of which are incorporated herein by reference.

TECHNICAL FIELD

The present invention relates to a filtration filter that filters filtration objects contained in a fluid.

BACKGROUND ART

As a method for filtering filtration objects contained in a fluid, a cross-flow filtration method has been known (see, for example, Japanese Unexamined Patent Application Publication No. 2013-210239 (Patent Document 1)). In the cross-flow filtration method disclosed in Patent Document 1, filtration is performed by causing a fluid to flow parallel to a membrane surface of a hollow fiber membrane.

SUMMARY OF INVENTION

Technical Problem

In recent years, a method for performing filtration by using a metallic porous membrane as a filtration filter has been known.

The present inventors have newly found a problem that when cross-flow filtration is performed using a metallic porous membrane as a filtration filter, if pressure is applied to the metallic porous membrane, the metallic porous membrane sometimes becomes detached from a frame member, so that it becomes impossible to hold the metallic porous membrane. In addition, in cross-flow filtration, when a step is present between a membrane surface of the metallic porous membrane and the frame member, that is, when a step is present in a flow passage, filtration objects become easy to adhere to the step in the flow passage. Thus, it becomes difficult to collect the filtration objects adhering to the step in the flow passage, resulting in reduction in the collection rate of the filtration objects. The present inventors have found that it is possible to prevent reduction in the collection rate of the filtration objects by reducing the size of the step between the membrane surface and the frame member. Therefore, the present inventor has arrived at the following invention.

It is an object of the present invention to provide a filtration filter having a structure suitable for the case of performing cross-flow filtration by using a metallic porous membrane.

BRIEF DESCRIPTION OF THE INVENTION

In an embodiment, a filtration filter comprises a metallic porous membrane having a center and upper and lower frames holding the metallic porous membrane there between. The metallic porous membrane has upper and lower opposed main surfaces, an inner membrane portion for filtering objects contained in a fluid, the inner membrane portion extending outwardly from the center of the metallic porous membrane and lying in a plane, and a held portion extending outwardly from an outer periphery of the inner membrane portion. The lower frame has a first edge. The upper frame has a second edge which is located inward of and below the first edge of the lower frame. The held portion is bent around the first and second edges in a zig zag manner.

The first edge is preferably formed between first and second surfaces of the lower frame and the second edge is preferably formed between first and second surfaces of the upper frame. The first surfaces of the upper and lower frames preferably lie parallel to the upper and lower surfaces of the metallic porous membrane. The upper surface of the metallic porous member preferably extends along the first surface of the upper frame and the lower surface of the metallic porous member preferably extends along the first surface of the lower frame. The upper frame preferably does not contact the lower surface of the metallic porous member.

In an embodiment, the first surface of the upper frame contacts a portion of the upper surface of the metallic porous member corresponding to the held portion but does not contact the portion of the upper surface of the metallic porous member corresponding to the inner membrane portion.

The upper frame preferably further includes a third surface extending parallel to its first surface. The second surface of the upper frame preferably faces the second surface of the lower frame with the held portion extending there between. The third surface of the upper frame preferably faces the first surface of the lower frame with the held portion extending there between. In this embodiment, the distance between the second surface of the upper frame and the second surface of the lower frame as measured in a direction parallel to the plane of the membrane portion is preferably greater than the distance between the third surface of the upper frame and the first surface of the lower frame a measured in a direction perpendicular to the plane of the membrane portion.

In another embodiment of the invention, the filtration filter comprises a metallic porous membrane having a center and upper and lower frames holding the metallic porous membrane there between. Like the foregoing embodiment, the metallic porous membrane has a center and includes upper and lower opposed main surfaces, an inner membrane portion for filtering objects contained in a fluid, the inner membrane portion extending outwardly from the center of the metallic porous membrane and lying in a plane, and a held portion extending outwardly from an outer periphery of the inner membrane portion. In this embodiment, the lower frame having first and second edges and the upper frame has first and second edges. The first edge of the upper frame is located inward of and below the first edge of the lower frame. The second edge of the upper frame is located outwardly of and above the first edge of the lower frame. The second edge of the lower frame is located outward of and above the second edge of the upper frame. The held portion is bent around the first, second, third and fourth edges in a zig zag manner.

Figure 1:
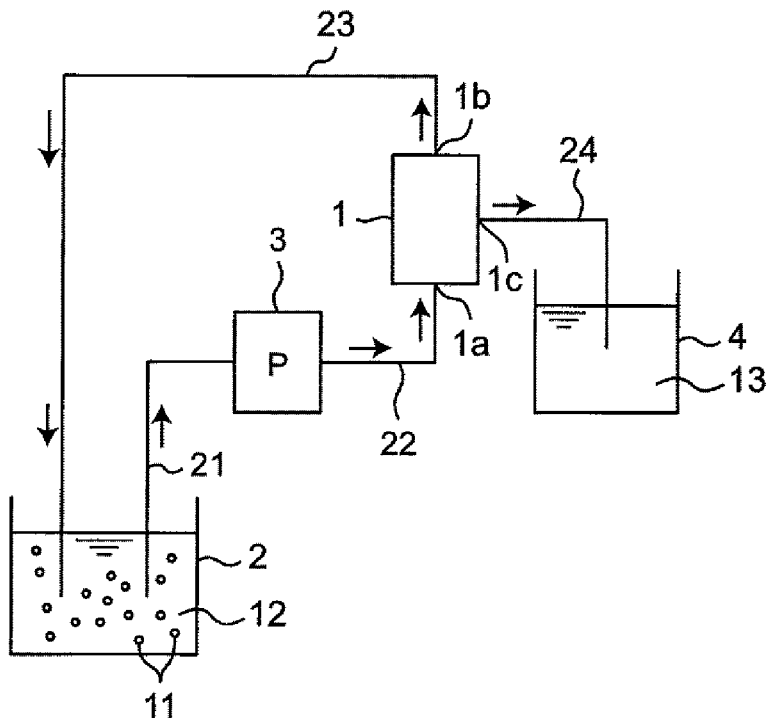
FIG. 1 is a schematic diagram showing a state where filtration objects is filtered by using a filtration device including a filtration filter of an embodiment 1 according to the present invention.

A filtration filter of an aspect of the present invention includes:

a metallic porous membrane having a membrane portion for filtering filtration objects contained in a fluid and a held portion provided at an outer periphery thereof; and a first frame member and a second frame member holding the held portion of the metallic porous membrane therebetween, wherein the held portion has a bent portion bent to a second principal surface side of the membrane portion opposing a first principal surface of the membrane portion, the first frame member is in contact with the held portion at the first principal surface side of the metallic porous membrane, and the second frame member is disposed at an inner side portion of the first frame member and is in contact with the held portion at the second principal surface side of the metallic porous membrane.

Because of such a configuration, it is possible to provide a filtration filter having a structure suitable for the case of performing cross-flow filtration by using a metallic porous membrane. For example, it is possible to firmly hold the metallic porous membrane by holding the held portion, which has the bent portion, between the first frame member and the second frame member. In addition, the first frame member is in contact with the held portion that is a portion at the outer peripheral side of the metallic porous membrane, and the second frame member is disposed at the inner side portion of the first frame member and is in contact with the held portion at the second principal surface side of the metallic porous membrane, whereby it is possible to reduce the size of a step between the first principal surface (membrane surface) of the metallic porous membrane and the first frame member. Therefore, an amount of filtration objects adhering to the step portion is reduced, so that the collection rate of the filtration objects increases.

The held portion may have a first bent portion bent to the second principal surface side of the membrane portion, and a second bent portion bent in an extending direction of the membrane portion at a position at an outer edge side of the metallic porous membrane with respect to the first bent portion, the second frame member may have a first step portion projecting toward the membrane portion, the first step portion may be in contact with the first bent portion, and the first frame member may be in contact with the second bent portion.

Because of such a configuration, since the first step portion of the second frame member is in contact with the first bent portion of the held portion and the first frame member is in contact with the second bent portion of the held portion, it is possible to further firmly fix the metallic porous membrane. As a result, it is possible to provide a filtration filter having a structure further suitable for the case of performing cross-flow filtration by using a metallic porous membrane.

The held portion may further have a third bent portion bent in a direction from the first principal surface of the membrane portion to the second principal surface of the membrane portion at a position at the outer edge side of the metallic porous membrane with respect to the second bent portion, and a fourth bent portion bent in the extending direction of the membrane portion, at a position at the outer edge side of the metallic porous membrane with respect to the third bent portion, the second frame member may have a second step portion projecting toward the held portion of the metallic porous membrane at a position at an outer edge side of the second frame member with respect to the first step portion, the first frame member may have a third step portion projecting toward the held portion of the metallic porous membrane at a position of an outer side portion with respect to the second step portion of the second frame member, the second step portion may be in contact with the third bent portion, and the third step portion may be in contact with the fourth bent portion.

Because of such a configuration, since the held portion having more bent portions is held between the first frame member and the second frame member, it is possible to further firmly fix the metallic porous membrane.

In a state where the held portion of the metallic porous membrane is held between the first frame member and the second frame member, a distance between the first frame member and the second frame member in an extending direction of the metallic porous membrane may be larger than a distance between the first frame member and the second frame member in a thickness direction of the metallic porous membrane.

Because of such a configuration, when the held portion of the metallic porous membrane is held between the first frame member and the second frame member, it is possible to form a gap for releasing deformation of the bent portion, between the first frame member and the second frame member in the extending direction of the metallic porous membrane. As a result, it is possible to firmly hold the held portion of the metallic porous membrane by the first frame member and the second frame member.

A distance between a first contact surface of the second frame member that is in contact with the first bent portion and a part of the membrane portion and a second contact surface of the second frame member that is in contact with the second bent portion may be substantially equal to a distance between a third contact surface of the first frame member that is in contact with the second bent portion and a bottom surface of the first frame member.

Because of such a configuration, it is possible to reduce the size of a step between the first principal surface of the metallic porous membrane and the bottom surface of the first frame member to make the first principal surface of the metallic porous membrane and the bottom surface of the first frame member substantially flush with each other.

Hereinafter, embodiments according to the present invention will be described with reference to the accompanying drawings. In addition, in each drawing, each element is shown in an exaggerated manner for easy explanation.

EMBODIMENT 1

[Entire Configuration]

FIG. 1 is a schematic diagram showing a state where filtration objects are filtered using a filtration device including a filtration filter of Embodiment 1 according to the present invention. As shown in FIG. 1, the filtration device 1 is a cross-flow filtration device which is configured to introduce a fluid 12 containing filtration objects 11 through a fluid introduction port 1a and discharge the fluid 12 through a fluid discharge port 1b. In addition, the filtration device 1 is configured to filter a part of the fluid 12 flowing from the fluid introduction port 1a to the fluid discharge port 1b and discharge a fluid (hereinafter, referred to as filtrate) 13 from which the filtration objects 11 have been removed through the filtration, through a filtrate discharge port 1c.

The fluid 12 containing the filtration objects 11 is contained in a fluid tank 2. The fluid 12 in the fluid tank 2 is sucked into a pump 3 through a pipe 21 and supplied to the fluid introduction port 1a of the filtration device 1 through a pipe 22 by the pump 3. The fluid 12 passing through the interior of the filtration device 1 and discharged through the fluid discharge port 1b is returned into the fluid tank 2 through a pipe 23. In this manner, while the pump 3 is driven, the fluid 12 circulates in order of the fluid tank 2, the pipe 21, the pump 3, the pipe 22, the filtration device 1, and the pipe 23.

A part of the fluid 12 supplied to the interior of the filtration device 1 is filtered and discharged as the filtrate 13 through the filtrate discharge port 1c. The filtrate 13 discharged through the filtrate discharge port 1c is placed in a filtrate tank 4 through a pipe 24.

As another embodiment of FIG. 1, the pump 3 may not be disposed between the pipe 21 and the pipe 22 and may be disposed in a passage in the pipe 23. Alternatively, the fluid tank 2 and the filtrate tank 4 may be configured as sealed tanks and a filtration device of a closed system may be achieved.

In Embodiment 1, the fluid 12 is preferably a liquid, and the filtration objects 11 are biological products contained in a liquid. In the present specification, the term "biological product" means a substance derived from organism such as cells (eukaryote), bacteria (eubacteria), and viruses. Examples of cells (eukaryote) include ova, sperms, induced pluripotent stem cells (iPS cells), ES cells, stem cells, mesenchymal stem cells, mononuclear cells, single cells, cell clusters, floating cells, adherent cells, nerve cells, leukocyte, lymphocyte, cells for regenerative medicine, autologous cells, cancer cells, circulating tumor cells (CTC), HL-60, HELA, and fungi. Examples of bacteria (eubacteria) include gram positive bacteria, gram negative bacteria, *Escherichia coli*, and *Mycobacterium* tuberculoses. Examples of viruses include DNA viruses, RNA viruses, rotaviruses, (avian) influenza viruses, yellow fever viruses, dengue fever viruses, encephalitis viruses, hemorrhagic fever viruses, and immunodeficiency viruses.

Alternatively, the fluid 12 is a gas, and the filtration objects 11 are particles contained in a gas. The particles mean industrial powder materials or PM2.5.

Figure 2:
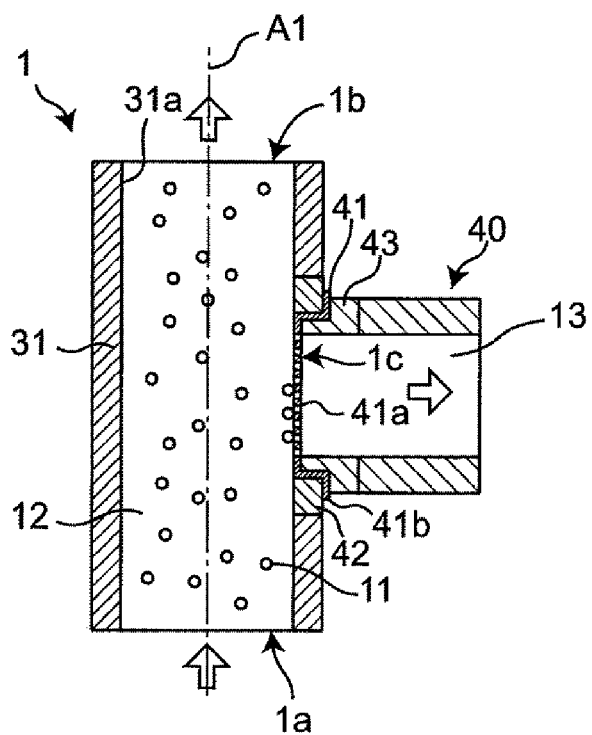
FIG. 2 is a schematic cross-sectional view of the filtration device in FIG. 1.

FIG. 2 is a schematic cross-sectional view of the filtration device 1. As shown in FIG. 2, the filtration device 1 includes: a tubular member 31 having a flow passage 31a through which the fluid 12 containing the filtration objects 11 flows and a filtration filter 40 for filtering the filtration objects 11.

The tubular member 31 is, for example, a cylindrical member. In Embodiment 1, the tubular member 31 is composed of a tubular member having a uniform inner diameter. The tubular member 31 has the fluid introduction port 1a, the fluid discharge port 1b, and the filtrate discharge port 1c. In Embodiment 1, the fluid introduction port 1a is provided in a lower portion of the tubular member 31, and the fluid discharge port 1b is provided in an upper portion of the tubular member 31. In addition, the filtrate discharge port 1c is provided in a part of a side wall of the tubular member 31.

The filtration filter 40 is attached to a part of the side wall of the tubular member 31. In Embodiment 1, the filtration filter 40 is attached at the filtrate discharge port 1c. The filtration filter 40 includes a metallic porous membrane 41 for filtering the filtration objects 11 and first and second frame members 42 and 43 that hold an outer peripheral portion of the metallic porous membrane 41 therebetween. In Embodiment 1, a flow direction of the fluid 12 is parallel to a direction in which a pipe axis A1 extends. The metallic porous membrane 41 is disposed parallel to the direction in which the pipe axis A1 extends. As another embodiment of the tubular member 31, the tubular member 31 may have any cross-sectional shape such as a quadrate shape or an elliptical shape. In addition, examples of the material of the tubular member 31 include stainless steel, silicone resin, PVDF (Teflon), vinyl chloride, glass, and butadiene-free resin. Furthermore, a coating material may be applied to the tubular member 31 such that filtration objects are less likely to adhere to these materials.

Figure 3:
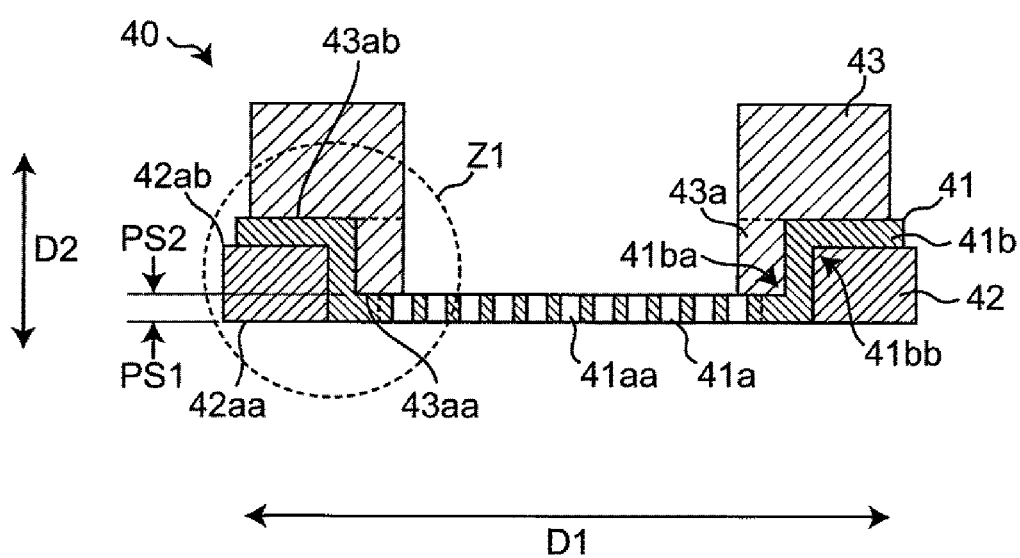
FIG. 3 is a schematic diagram showing the configuration of the filtration filter of Embodiment 1 according to the present invention.

Next, the configuration of the filtration filter 40 will be described in detail. FIG. 3 is a schematic diagram showing the configuration of the filtration filter 40.

<Metallic Porous Membrane>

The metallic porous membrane 41 is a membrane for separating the filtration objects 11 from the fluid 12. As shown in FIG. 3, the metallic porous membrane 41 is, for example, a circular metallic mesh having a first principal surface PS1 and a second principal surface PS2 opposing each other. In the present specification, the first principal surface PS1 is a principal surface of the metallic porous membrane 41 that is located at the flow passage 31a side of the tubular member 31. The second principal surface PS2 is a principal surface of the metallic porous membrane 41 that is located at the filtrate discharge port 1c side of the tubular member 31.

Examples of the material of the metallic porous membrane 41 include gold, silver, copper, platinum, nickel, stainless steel, palladium, titanium, cobalt, and alloys thereof. The diameter of the metallic porous membrane 41 is, for example, 8 mm. The thickness of the metallic porous membrane 41 is, for example, not less than 0.05 μm and not greater than 100 μm, and preferably not less than 0.1 μm and not greater than 50 μm. The outer shape of the metallic porous membrane 41 may be, for example, any of a circular shape, an elliptical shape, and a polygonal shape.

The metallic porous membrane 41 includes a membrane portion 41a having a plurality of through holes 41aa and a held portion 41b provided at the outer peripheral portion thereof.

Figure 4:
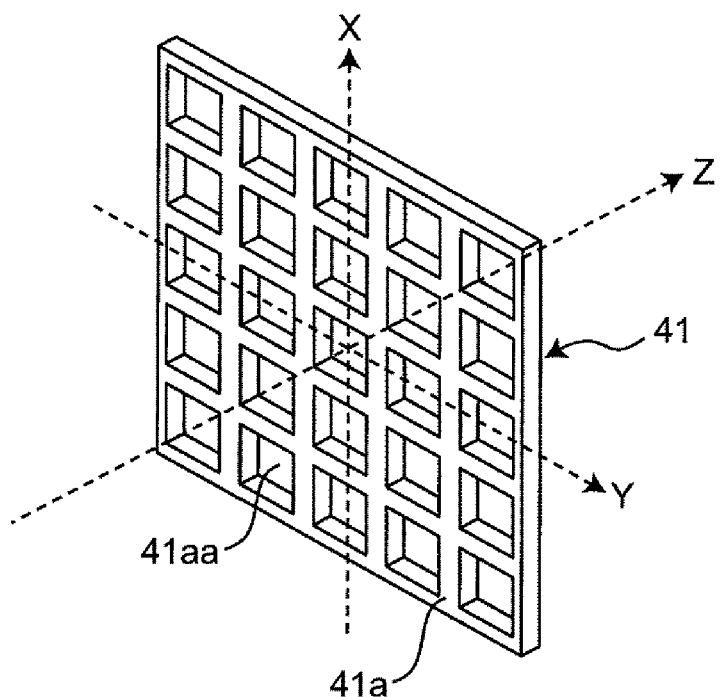
FIG. 4 is a partially enlarged perspective view of a membrane portion of a metallic porous membrane in Embodiment 1 according to the present invention.

FIG. 4 is a partially enlarged perspective view of the membrane portion 41a of the metallic porous membrane 41. An X direction, a Y direction, and a Z direction in FIG. 4 are a vertical direction, a horizontal direction, and a thickness direction of the metallic porous membrane 41, respectively. As shown in FIG. 4, the membrane portion 41a has the plurality of through holes 41aa penetrating the first and second principal surfaces PS1 and PS2 of the membrane portion 41a. The membrane portion 41a is preferably a plate-like structure (grid-like structure) in which the plurality of through holes 41aa are arranged at regular intervals in a matrix manner.

Figure 5:
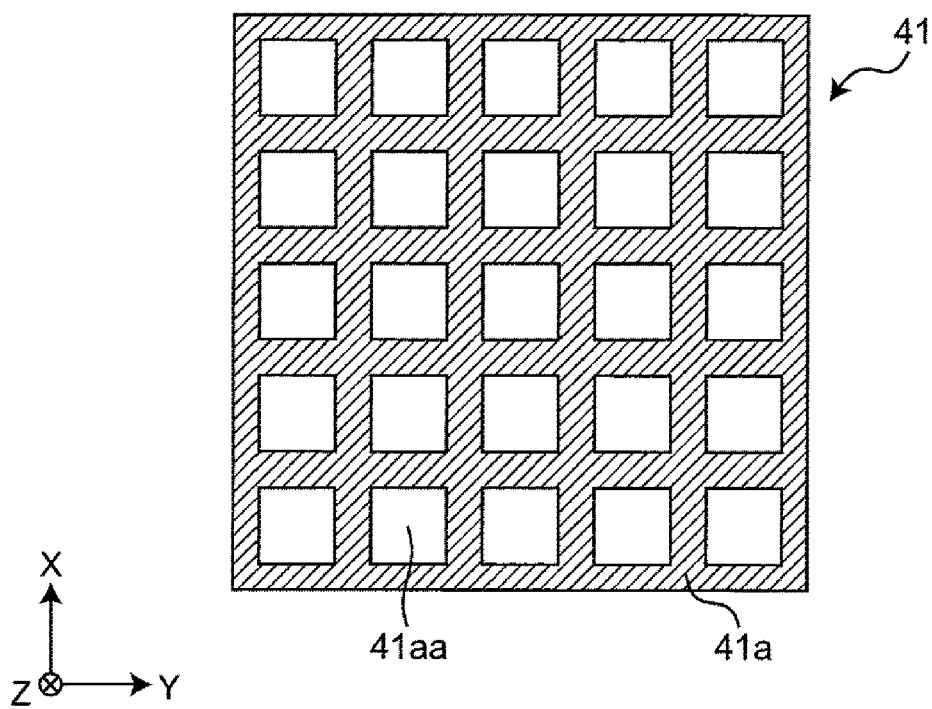
FIG. 5 is a schematic diagram of a part of the membrane portion of the metallic porous membrane in FIG. 4, as seen from a thickness direction.

FIG. 5 is a schematic diagram of a portion of the membrane portion 41a of the metallic porous membrane 41 in FIG. 4, as seen from the thickness direction. As shown in FIG. 5, the plurality of through holes 41aa each have a square shape as seen from the first principal surface PS1 side of the membrane portion 41a of the metallic porous membrane 41, that is, as seen in the Z direction. The plurality of through holes 41aa are provided at equal intervals in two arrangement directions parallel to the respective sides of the square, that is, in the X direction and the Y direction in FIG. 5. The shape of each through hole 41aa is not limited to a square shape, and may be, for example, a rectangular shape, a circular shape, or an elliptical shape. In addition, the arrangement of the holes is not limited to a square grid arrangement, and may be, for example, a rectangular arrangement in which intervals in two arrangement directions are not equal to each other as long as the arrangement is a quadrate arrangement, or may be a triangular grid arrangement or a quasiperiodic arrangement.

The shape and the dimension of each through hole 41aa are designed, as appropriate, in accordance with the sizes and the shapes of the filtration objects 11 to be filtered. In Embodiment 1, the size of each through hole 41aa is, for example, not less than 0.1 μm and not greater than 500 μm in vertical size, and is not less than 0.1 and not greater than 500 μm in horizontal size. The intervals between the through holes 41aa are each, for example, greater than 1 time of the opening diameter of the through hole 41aa and not greater than 10 times of the opening diameter, and more preferably not greater than 3 times of the opening diameter. In addition, the opening proportion of the through holes 41aa in the membrane portion 41a of the metallic porous membrane 41 is, for example, not less than 10%.

As shown in FIG. 3, the held portion 41b is formed by bending the outer peripheral portion of the metallic porous membrane 41 towards the second principal surface PS2 side. The held portion 41b is a portion at an outer edge side of the metallic porous membrane 41 from a position in the membrane portion 41a at which bending starts. In Embodiment 1, the held portion 41b has a first bent portion 41ba and a second bent portion 41bb. The first bent portion 41ba is a portion of the membrane portion 41a that is bent toward the second principal surface PS2 side. The second bent portion 41bb is a portion that is formed at the outer edge side of the metallic porous membrane 41 with respect to the first bent portion 41ba and is bent in a direction D1 extending away from the membrane portion 41a. In Embodiment 1, the first bent portion 41ba is bent in a direction from the first principal surface PS1 of the membrane portion 41a to the second principal surface PS2 of the membrane portion 41a. In addition, the second bent portion 41bb is bent so as to be parallel to the first principal surface PS1 and the second principal surface PS2 of the membrane portion 41a. Therefore, in a portion from the first bent portion 41ba to the second bent portion 41bb, the held portion 41b extends in the direction from the first principal surface PS1 of the membrane portion 41a to the second principal surface PS2 of the membrane portion 41a. In addition, in a portion at the outer edge side of the metallic porous membrane 41 with respect to the second bent portion 41bb, the held portion 41b extends in the extending direction D1 of the membrane portion 41a, that is, parallel to the first principal surface PS1 and the second principal surface PS2 of the membrane portion 41a. The extending direction D1 of the membrane portion 41a of the metallic porous membrane 41 includes a direction toward the outer edge side of the metallic porous membrane 41 and a direction toward a side opposite to the outer edge of the metallic porous membrane 41. In Embodiment 1, as described above, the second bent portion 41bb of the held portion 41b is bent in the direction toward the outer edge side of the metallic porous membrane 41 with respect to the first bent portion 41ba. Alternatively, each of the first bent portion 41ba and the second bent portion 41bb may be, for example, a portion bent in an arc shape, or a portion bent at an obtuse angle.

<First Frame Member>

The first frame member 42 is a frame that holds the held portion 41b of the metallic porous membrane 41 between the second frame member 43 and this frame. Specifically, the first frame member 42 is preferably formed in a loop shape (e.g., an annular shape) so as to receive the second frame member 43 with the held portion 41b of the metallic porous membrane 41 interposed therebetween. The first frame member 42 is located at the outer edge side of the metallic porous membrane 41 with respect to the boundary between the membrane portion 41a and the held portion 41b and is in contact with the held portion 41b at the first principal surface PS1 side of the metallic porous membrane 41. The boundary between the membrane portion 41a and the held portion 41b is a position in the outer peripheral portion of the metallic porous membrane 41 at which bending to the second principal surface PS2 side starts. In Embodiment 1, the first frame member 42 is located in the extending direction D1 (FIG. 3) with respect to the bent position of the first bent portion 41ba and is in contact with the held portion 41b but is not in contact with the membrane portion 41a, at the first principal surface PS1 side of the metallic porous membrane 41. The first frame member 42 is attached to the side wall of the tubular member 31.

<Second Frame Member>

The second frame member 43 is a frame that holds the held portion 41b of the metallic porous membrane 41 between the first frame member 42 and this frame. Specifically, the second frame member 43 is formed in a loop shape (e.g., an annular shape). In addition, a first step portion 43a is provided at an inner peripheral portion of the second frame member 43 so as to project toward a part of the membrane portion 41a of the metallic porous membrane 41. The second frame member 43 is disposed at an inner side portion of the first frame member 42 with the held portion 41b of the metallic porous membrane 41 interposed therebetween. The second frame member 43 is formed such that the first step portion 43a is fitted at the inner side portion of the first frame member 42. That is, the second frame member 43 is in contact with the held portion 41b and the part of the membrane portion 41a at the second principal surface PS2 side of the metallic porous membrane 41.

In Embodiment 1, the second frame member 43 is connected to the pipe 24 (FIG. 1).

The second frame member 43 is able to define the position of the first principal surface PS1 of the membrane portion 41a by pushing the membrane portion 41a in the direction from the second principal surface PS2 to the first principal surface PS1 with the first step portion 43a.

Examples of the materials that can be used for the first and second frame members 42 and 43 include metals such as duralumin and aluminum and resins such as polyethylene, polystyrene, polypropylene, polycarbonate, polyacetal, polyether imide, acrylic resin, and polylactic acid.

Next, a detailed mechanism that holds the metallic porous membrane 41 by the first frame member 42 and the second frame member 43, will be described.

Figure 6:
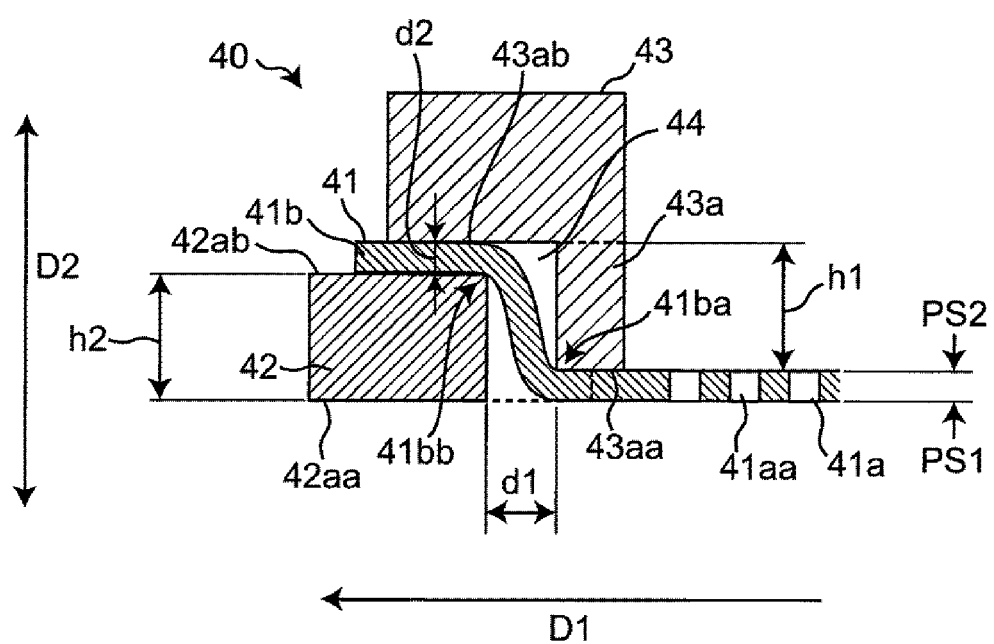
FIG. 6 is an enlarged view of a portion Z1 in FIG. 3.

FIG. 6 is an enlarged diagram of a portion Z1 of the filtration filter 40 in FIG. 3. As shown in FIG. 6, a contact surface 43aa of the first step portion 43a of the second frame member 43 is in contact with the part of the membrane portion 41a in a state where the held portion 41b of the metallic porous membrane 41 is held between the first frame member 42 and the second frame member 43. Accordingly, the membrane portion 41a is pushed by the contact surface 43aa of the first step portion 43a in the direction from the second principal surface PS2 to the first principal surface PS1. In this state, the first bent portion 41ba of the held portion 41b contacts a corner portion of the first step portion 43a of the second frame member 43 and force is applied to the held portion 41b in the direction from the second principal surface PS2 of the membrane portion 41a to the first principal surface PS1 of the membrane portion 41a. In this manner, the corner portion of the first step portion 43a of the second frame member 43 supports the held portion 41b at the first bent portion 41ba in the direction from the second principal surface PS2 of the membrane portion 41a to the first principal surface PS1 of the membrane portion 41a.

Next, at the second bent portion 41bb which is formed at the outer edge side of the metallic porous membrane 41 with respect to the first bent portion 41ba, the held portion 41b is in contact with a corner portion of the first frame member 42. In this state, the corner portion of the first frame member 42 is in contact with the second bent portion 41bb, and force is applied to the held portion 41b in the direction from the first principal surface PS1 of the membrane portion 41a to the second principal surface PS2 of the membrane portion 41a. In this manner, the corner portion of the first frame member 42 supports the held portion 41b at the second bent portion 41bb in the direction from the first principal surface PS1 of the membrane portion 41a to the second principal surface PS2 of the membrane portion 41a.

Next, the held portion 41b, which extends in the extending direction D1 of the membrane portion 41a at the outer edge side of the metallic porous membrane 41 with respect to the second bent portion 41bb, is held between a contact surface 42ab of the first frame member 42 and a contact surface 43ab of the second frame member 43.

As described above, in the filtration filter 40, it is possible to apply sufficient tension for holding the metallic porous membrane 41 by the metallic porous membrane 41 being supported with the forces in the different directions from each other in a thickness direction D2 of the membrane portion 41a at the first bent portion 41ba and the second bent portion 41bb of the held portion 41b.

In addition, as shown in FIG. 6, in Embodiment 1, a distance d1 between the first frame member 42 and the second frame member 43 in the extending direction D1 of the metallic porous membrane 41 is designed so as to be larger than a distance d2 between the first frame member 42 and the second frame member 43 in the thickness direction D2 of the metallic porous membrane 41 in the state where the held portion 41b of the metallic porous membrane 41 is held between the first frame member 42 and the second frame member 43. By so designing, it is possible to form a gap 44 between the left hand side of the step portion 43a and the second principal surface PS2 of the held portion 41b located between the first bent portion 41ba and the second bent portion 41bb. By providing the gap 44, it is possible to release deformation of the held portion 41b occurring when the held portion 41b of the metallic porous membrane 41 is held between the first frame member 42 and the second frame member 43. The distance d1 is, for example, larger than the distance d2 and smaller than 100 times of the distance d2.

Next, a detailed mechanism that defines the position of the first principal surface PS1 of the membrane portion 41a of the metallic porous membrane 41 by the first step portion 43a of the second frame member 43, will be described.

As shown in FIG. 6, the first step portion 43a projects downwardly (as viewed in FIG. 6) toward the portion of membrane portion 41a located below it and the contact surface 43aa pushes down on the second principal surface PS2 towards the first principal surface PS1. The second frame member 43 is not in contact with the first principal surface PS1 of the first frame member 42. Since the position of the membrane portion 41a is not limited by the first frame member 42, it is possible to freely set a held position of the membrane portion 41a by changing a height h1 of the first step portion 43a of the second frame member 43. That is, it is possible to freely set the position of the first principal surface PS1 of the membrane portion 41a by changing the height h1 of the first step portion 43a of the second frame member 43. In the present specification, the height h1 of the first step portion 43a means the distance between the first contact surface 43aa of the first step portion 43a of the second frame member 43 and the second contact surface 43ab of the second frame member 43.

In Embodiment 1, the height of the first step portion 43a is set such that the first principal surface PS1 of the membrane portion 41a and a bottom surface 42aa of the first frame member 42 are substantially flush with each other. Specifically, the height h1 of the first step portion 43a is substantially equal to a distance h2 between the third contact surface 42ab of the first frame member 42 and the bottom surface 42aa of the first frame member. Here, being substantially equal to means that the difference between the distance h1 and the distance h2 is within a range of ±10%. The shape of the frame member is not limited to an annular shape and may be any shape such as a quadrate shape and a polygonal shape.

Advantageous Effects

With the filtration filter 40 according to Embodiment 1, it is possible to achieve the following advantageous effects.

In the filtration filter 40, the first frame member 42 and the second frame member 43 are disposed so as to oppose each other with the held portion 41b interposed therebetween at the outer edge side of the metallic porous membrane 41 with respect to the first bent portion 41ba. That is, the held portion 41b, which is provided at the outer peripheral portion of the metallic porous membrane 41 and has the first bent portion 41*ba* and the second bent portion 41*bb*, is held between the first frame member 42 and the second frame member 43. At the outer edge side of the metallic porous membrane 41 with respect to the boundary between the membrane portion 41*a* and the held portion 41*b*, the first frame member 42 is in contact with the held portion 41*b* at the first principal surface PS1 side of the metallic porous membrane 41, and the second frame member 43 is in contact with the held portion 41*b* and the part of the membrane portion 41*a* at the second principal surface PS2 side of the metallic porous membrane 41. Because of such a configuration, it is possible to firmly hold the outer peripheral portion of the metallic porous membrane 41 by the first and second frame members 42 and 43. Thus, it is possible to provide the filtration filter 40 suitable for a cross-flow filtration method.

In the filtration filter 40, the second frame member 43 has the first step portion 43*a* projecting toward the part of the membrane portion 41*a*. Thus, in the state where the held portion 41*b* of the metallic porous membrane 41 is held between the first frame member 42 and the second frame member 43, it is possible to bring the first bent portion 41*ba* into contact with the first step portion 43*a* of the second frame member 43 and bring the second bent portion 41*bb* into contact with the first frame member 42. Because of such a configuration, it is possible to apply tension to the held portion 41*b* and hold the held portion 41*b*. Even when a fluid passes through the metallic porous membrane 41 and pressure is applied to the metallic porous membrane 41, it is possible to firmly hold the first bent portion 41*ba* and the second bent portion 41*bb* by the first frame member 42 and the second frame member 43.

In addition, the contact surface 43*aa* of the first step portion 43*a* of the second frame member 43 is in contact with the part of the membrane portion 41*a* so as to push the membrane portion 41*a* in the direction from the second principal surface PS2 to the first principal surface PS1. Since the first frame member 42 is not disposed at the first principal surface PS1 side of the membrane portion 41*a*, it is possible to freely define the position of the first principal surface PS1, which is the membrane surface of the membrane portion 41*a*, by setting the height h1 of the first step portion 43*a*. That is, it is possible to freely define the position of the first principal surface PS1 of the membrane portion 41*a* by changing the distance between the first contact surface 43*aa* of the first step portion 43*a* of the second frame member 43, which is in contact with the first bent portion 41*ba* and the part of the membrane portion 41*a*, and the second contact surface 43*ab* of the second frame member 43, which is in contact with the second bent portion 41*bb*. As a result, it is possible to reduce the size of the step between the first principal surface PS1 of the membrane portion 41*a* and the bottom surface 42*aa* of the first frame member 42.

In the filtration filter 40, the height h1 of the first step portion 43*a* is set so as to be substantially equal to the distance h2 between the third contact surface 42*ab* of the first frame member 42, which is in contact with the second bent portion 41*bb*, and the bottom surface 42*aa* of the first frame member. Because of such a configuration, it is possible to make the first principal surface PS1 of the membrane portion 41*a* and the bottom surface 42*aa* of the first frame member 42 substantially flush with each other.

In the filtration filter 40, the gap 44 is formed between the first frame member 42 and the first step portion 43*a* of the second frame member 43 in the state where the held portion 41*b* of the metallic porous membrane 41 is held between the first frame member 42 and the second frame member 43. The distance of the gap 44 is designed so as to be larger than the distance of the gap between the first frame member 42 and the second frame member 43 in the thickness direction D2 of the metallic porous membrane 41. Because of such a configuration, it is possible to release deformation of the held portion 41*b* occurring when the held portion 41*b* of the metallic porous membrane 41 is held between the first frame member 42 and the second frame member 43.

In Embodiment 1, FIG. 2 shows the example in which the tubular member 31 has a straight cylindrical shape (straight tubular shape), but the present invention is not limited thereto. The tubular member 31 only needs to be configured to be able to allow the fluid 12 to flow along the membrane portion 41*a* of the metallic porous membrane 41. For example, as shown in FIGS. 10 to 13, a portion of the tubular member 31 at the fluid introduction port 1*a* side or the fluid discharge port 1*b* side may be configured to be bent in a direction that intersects the extending direction of the pipe axis A1.

Figure 14:
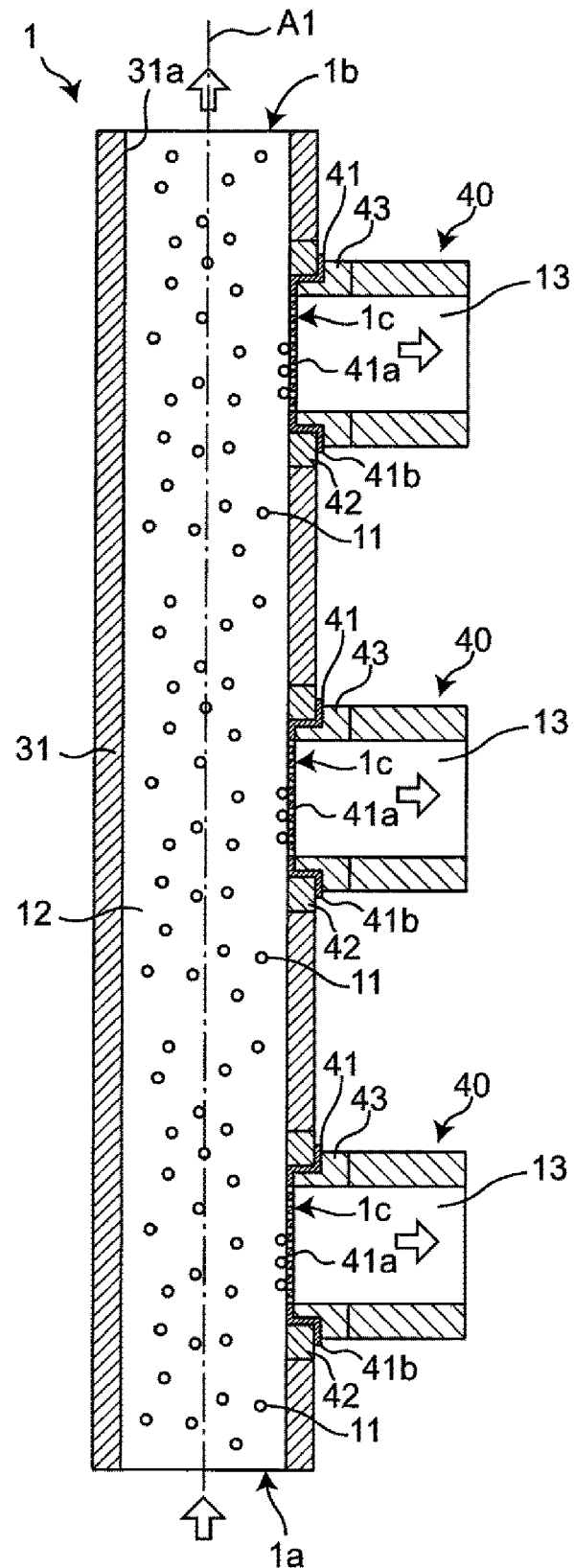
FIG. 14 is a cross-sectional view showing an example in which a plurality of the filtration filters of Embodiment 1 according to the present invention are provided to one tubular member.

In Embodiment 1, FIG. 2 shows an example in which a single filtration filter 40 is provided to the one tubular member 31, but the present invention is not limited thereto. As shown in FIG. 14, a plurality of filtration filters 40 (e.g., three filtration filters 40) may be provided to the one tubular member 31. In this case, the plurality of filtration filters 40 are preferably arranged in the extending direction of the pipe axis A1 as shown in FIG. 14. In addition, the through holes 41*aa* of the membrane portions 41*a* of the metallic porous membranes 41 of the plurality of filtration filters 40 may have opening diameters different from each other. With this configuration, even in the case where a plurality of filtration objects 11 having different sizes are contained in the fluid 12, it is possible to size these filtration objects 11.

Figure 7:
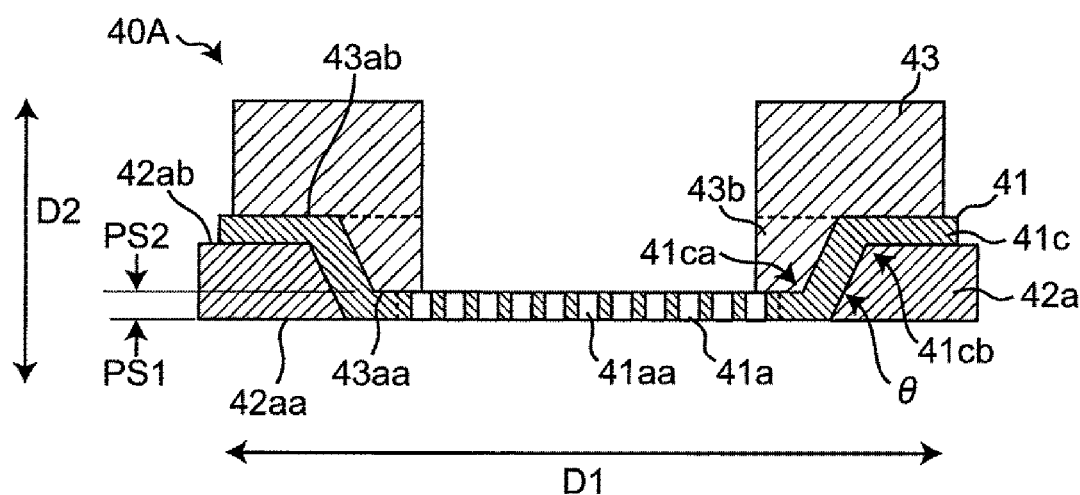
FIG. 7 is a diagram showing a modification of the filtration filter of Embodiment 1 according to the present invention.

In Embodiment 1, the example has been described in which the first bent portion 41*ba* is bent in the direction from the first principal surface PS1 of the membrane portion 41*a* to the second principal surface PS2 of the membrane portion 41*a*, but the present invention is not limited thereto. The first bent portion 41*ba* only needs to be bent to the second principal surface PS2 side of the membrane portion 41*a* so as to be supported by the corner portion of the first step portion 43*a* of the second frame member 43, and may be bent obliquely relative to the first principal surface PS1 and the second principal surface PS2. FIG. 7 is a diagram showing a filtration filter 40A of a modification. As shown in FIG. 7, in the filtration filter 40A, a first bent portion 41*ca* of a held portion 41*c* is bent at an inclination angle θ relative to the first principal surface PS1. In the filtration filter 40A, a first frame member 42*a* and a first step portion 43*b* of the second frame member 43 are configured with a shape corresponding to the inclination of the held portion 41*c*. Specifically, the surface of the first frame member 42*a* at the first bent portion 41*ca* side is formed so as to be inclined at the angle θ. In addition, the first step portion 43*b* is formed in a trapezoidal shape along the bent shape of the held portion 41*c*. Because of such a configuration, the first bent portion 41*ca* is easily supported by the first step portion 43*b* of the second frame member 43, and a second bent portion 41*cb* is easily supported by the first frame member 42. Thus, in the filtration filter 40A, it is possible to more firmly fix the metallic porous membrane 41 by the first frame member 42*a* and the second frame member 43.

In Embodiment 1, the example has been described in which the second bent portion 41*bb* is bent in the extending direction D1 of the membrane portion 41*a*, but the present invention is not limited thereto. The second bent portion 41bb only needs to be supported by the corner portion of the first frame member 42, and may be inclined in an oblique direction relative to the extending direction D1 of the membrane portion 41a.

In Embodiment 1, the example has been described in which the second bent portion 41bb of the held portion 41b is bent in the direction toward the outer edge side of the metallic porous membrane 41, but the present invention is not limited thereto. For example, the second bent portion 41bb may be bent to the side opposite to the outer edge of the metallic porous membrane 41.

In Embodiment 1, the configuration has been described in which the first frame member 42 is in contact with the held portion 41b at the first principal surface PS1 side of the metallic porous membrane 41 at the outer edge side of the metallic porous membrane 41 with respect to the boundary between the membrane portion 41a and the held portion 41b, but the present invention is not limited thereto. For example, the first frame member 42 may be in contact with the held portion 41b at the upper side (the second principal surface PS2 side) of the membrane portion 41a with respect to the first principal surface PS1.

In Embodiment 1, the configuration has been described in which the second frame member 43 is in contact with the held portion 41b and the part of the membrane portion 41a at the second principal surface PS2 side of the metallic porous membrane 41, but the present invention is not limited thereto. For example, the second frame member 43 may be configured to be in contact with only the held portion 41b without being in contact with the membrane portion 41a.

In Embodiment 1, the configuration has been described in which the first frame member 42 is formed of a member separate from the tubular member 31, but the present invention is not limited thereto. For example, the first frame member 42 may be formed so as to be integrated with the tubular member 31. Similarly, the configuration has been described in which the second frame member 43 is formed of a member separate from the tubular member 31, but the present invention is not limited thereto. For example, the second frame member 43 may be formed so as to be integrated with the tubular member 31 at the filtrate discharge port 1c side. Because of such a configuration, it is possible to reduce the number of components and provide the filtration filter 40 at low cost.

In Embodiment 1, the first frame member 42 and the second frame member 43 may be held by a first housing and a second housing that are fitted to each other. For example, the first housing and the second housing may be configured to be fitted to each other by a plurality of projections being inserted into a plurality of through holes. Specifically, the plurality of projections are arranged annularly on the first housing. Meanwhile, the plurality of through holes are provided annularly in the second housing in corresponding relation to the positions of the plurality of projections of the first housing, respectively. By fitting the first housing and the second housing to each other as described above, the held portion 41b of the metallic porous membrane 41 may be held between the first frame member 42 and the second frame member 43. In addition, the first housing and the second housing may be formed so as to be integrated with the first frame member 42 and the second frame member 43, respectively.

EMBODIMENT 2

[Entire Configuration]

A filtration filter of Embodiment 2 according to the present invention will be described with reference to FIG. 8.

Figure 8:
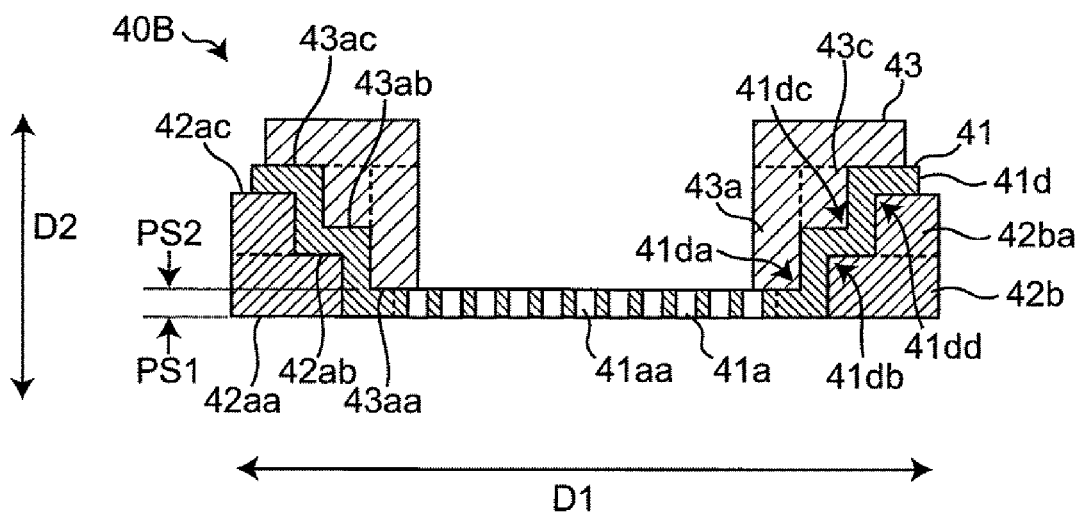
FIG. 8 is a diagram showing the configuration of a filtration filter of Embodiment 2 according to the present invention.

FIG. 8 shows a schematic configuration of a filtration filter 40B of Embodiment 2. In Embodiment 2, the differences from Embodiment 1 will be mainly described. In Embodiment 2, components that are the same as or equivalent to those in Embodiment 1 are designated by the same reference signs or similar reference signs and described. In addition, in Embodiment 2, the description overlapping Embodiment 1 is omitted.

As shown in FIG. 8, the filtration filter 40B of Embodiment 2 is different from the filtration filter 40 of Embodiment 1 in that a held portion 41d of the metallic porous membrane 41 has a third bent portion 41dc and a fourth bent portion 41dd. In addition, the filtration filter 40B of Embodiment 2 is different from the filtration filter 40 of Embodiment 1 in that the second frame member 43 has a second step portion 43c and a first frame member 42b has a third step portion 42ba.

In the filtration filter 40B, the held portion 41d includes, in addition to a first bent portion 41da and a second bent portion 41db, the third bent portion 41dc and the fourth bent portion 41dd.

The first bent portion 41da and the second bent portion 41db may be formed in the same manner as the first bent portion 41ba and the second bent portion 41bb of Embodiment 1. In Embodiment 2, the first bent portion 41da is bent in the direction from the first principal surface PS1 of the membrane portion 41a to the second principal surface PS2 of the membrane portion 41a. In addition, the second bent portion 41db is formed at the outer edge side of the metallic porous membrane 41 with respect to the first bent portion 41da and is bent in the extending direction D1 of the membrane portion 41a.

The third bent portion 41dc is formed at the outer edge side of the metallic porous membrane 41 with respect to the second bent portion 41db and is bent in the direction from the first principal surface PS1 of the membrane portion 41a to the second principal surface PS2 of the membrane portion 41a. The fourth bent portion 41dd is formed at the outer edge side of the metallic porous membrane 41 with respect to the third bent portion 41dc and is bent in the extending direction D1 of the membrane portion 41a.

The second frame member 43 has the second step portion 43c in addition to the first step portion 43a. The second step portion 43c is provided at an outer side portion with respect to the first step portion 43a. That is, the second step portion 43c is provided at the outer edge side of the metallic porous membrane 41 with respect to the first step portion 43a. The second step portion 43c is formed so as to project toward the held portion 41d at the second principal surface PS2 side of the metallic porous membrane 41. Specifically, the second step portion 43c projects toward the portion of the held portion 41d between the second bent portion 41db and the third bent portion 41dc.

The first frame member 42b has the third step portion 42ba. The third step portion 42ba is formed at an outer side portion with respect to the second step portion 43c of the second frame member 43. The third step portion 42ba is formed so as to project toward the held portion 41d at the first principal surface PS1 side of the metallic porous membrane. Specifically, the third step portion 42ba projects toward the portion of the held portion 41d between the fourth bent portion 41dd and the outer edge of the metallic porous membrane 41. In Embodiment 2, the first frame member 42b is formed, for example, in an L shape.

In filtration filter 40B, similarly to Embodiment 1, the first bent portion 41da is in contact with the first step portion 43a of the second frame member 43, and the second bent portion 41db is in contact with the first frame member 42b. Specifically, the first bent portion 41da is supported by the corner portion of the first step portion 43a of the second frame member 43, and the second bent portion 41db is supported by a corner portion of the first frame member 42b. In this case, at the first bent portion 41da, force is applied by the corner portion of the first step portion 43a of the second frame member 43 in the direction from the second principal surface PS2 of the membrane portion 41a to the first principal surface PS1 of the membrane portion 41a. Meanwhile, at the second bent portion 41db, force is applied by the corner portion of the first frame member 42b in the direction from the first principal surface PS1 of the membrane portion 41a to the second principal surface PS2 of the membrane portion 41a.

The third bent portion 41dc is in contact with the second step portion 43c of the second frame member 43. Specifically, the third bent portion 41dc is supported by a corner portion of the second step portion 43c, and force is applied thereto in the direction from the second principal surface PS2 of the membrane portion 41a to the first principal surface PS1 of the membrane portion 41a. Therefore, the held portion 41d is supported at the third bent portion 41dc by the corner portion of the second step portion 43c of the second frame member 43 in the direction from the second principal surface PS2 of the membrane portion 41a to the first principal surface PS1 of the membrane portion 41a.

The fourth bent portion 41dd is in contact with a third step portion 43ba of the first frame member 42b. Specifically, the fourth bent portion 41dd is supported by a corner portion of the third step portion 43ba, and force is applied thereto in the direction from the first principal surface PS1 of the membrane portion 41a to the second principal surface PS2 of the membrane portion 41a. Therefore, the held portion 41d is supported at the fourth bent portion 41dd in the direction from the first principal surface PS1 of the membrane portion 41a to the second principal surface PS2 of the membrane portion 41a.

The held portion 41d that extends in the extending direction D1 of the membrane portion 41a at the outer edge side of the metallic porous membrane 41 with respect to the fourth bent portion 41dd is held between a contact surface 42ac of the third step portion 42ba of the first frame member 42b and a contact surface 43ac of the second frame member 43. That is, the held portion 41d that is an outer side portion with respect to the fourth bent portion 41dd is held by the contact surface 42ac of the first frame member 42 and the contact surface 43ac of the second frame member 43.

Advantageous Effects

With the filtration filter 40B according to Embodiment 2, it is possible to achieve the following advantageous effects.

In the filtration filter 40B, the held portion 41d, which has the first bent portion 41da, the second bent portion 41db, the third bent portion 41dc, and the fourth bent portion 41dd, is held between the first frame member 42b and the second frame member 43. Because of such a configuration, it is possible to increase the number of locations at which the held portion 41d is supported by the first frame member 42b and the second frame member 43. Therefore, as compared to Embodiment 1, it is possible to more firmly fix the metallic porous membrane 41 by the first frame member 42b and the second frame member 43, and it is possible to provide the filtration filter 40B more suitable for a cross-flow filtration method.

Also in the filtration filter 40B, similarly to Embodiment 1, by changing the distance between the first contact surface 43aa of the first step portion 43a of the second frame member 43, which is in contact with the first bent portion 41da and a part of the membrane portion 41a, and the second contact surface 43ab of the second frame member 43, which is in contact with the second bent portion 41db, it is possible to freely define the position of the first principal surface PS1 of the membrane portion 41a. As a result, it is possible to reduce the size of the step between the first principal surface PS1 of the membrane portion 41a and the bottom surface 42aa of the first frame member 42.

The example has been described in which the held portion 41d has four bent portions in the filtration filter 40B, but the present invention is not limited thereto. For example, the held portion 41d may have five or more bent portions. By increasing the number of bent portions, it is possible to further firmly fix the metallic porous membrane 41 by the first frame member 42b and the second frame member 43.

In Embodiment 2, the example has been described in which the third bent portion 41dc is bent in the direction from the first principal surface PS1 of the membrane portion 41a to the second principal surface PS2 of the membrane portion 41a, but the present invention is not limited thereto. The third bent portion 41dc only needs to be supported by the corner portion of the second step portion 43c of the second frame member 43, and may be bent so as to be inclined obliquely relative to the direction from the first principal surface PS1 to the second principal surface PS2. In addition, the example has been described in which the fourth bent portion 41dd is bent in the extending direction of the membrane portion 41a, but the present invention is not limited thereto. The fourth bent portion 41dd only needs to be supported by the corner portion of the third step portion 42ba of the first frame member 42b, and may be inclined in an oblique direction relative to the extending direction of the membrane portion 41a.

Figure 9:
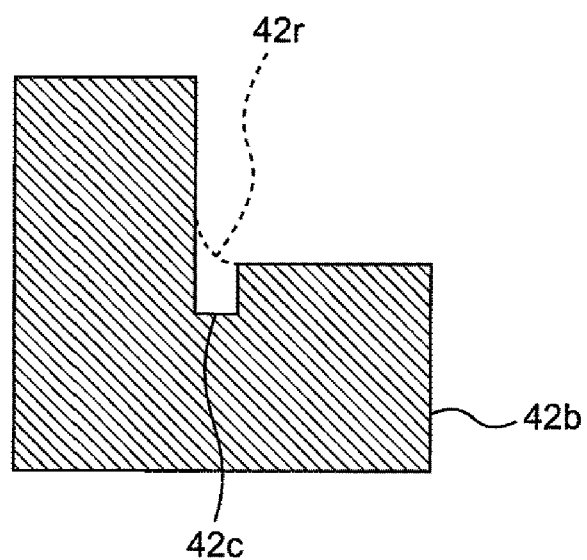
FIG. 9 is a diagram showing a modification of a first frame member of the filtration filter of Embodiment 2 according to the present invention.
Figure 10:
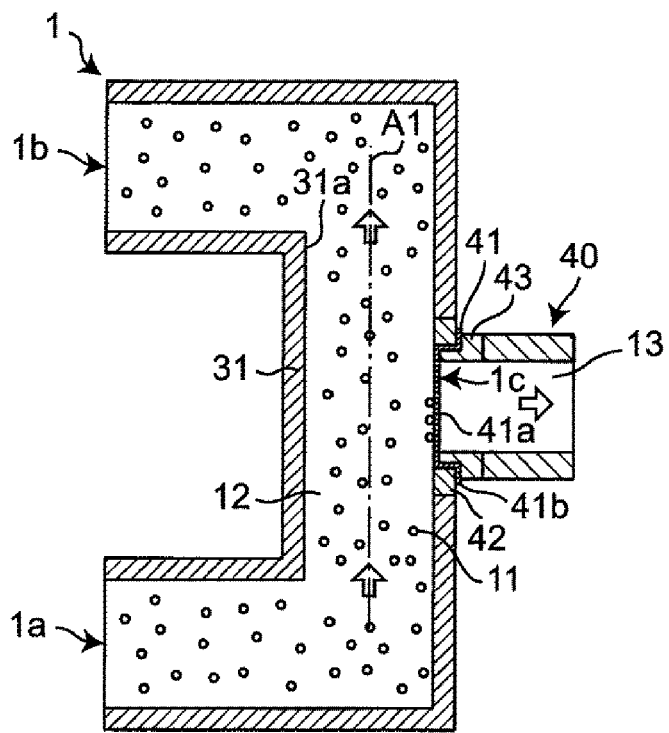
FIG. 10 is a cross-sectional view showing a modification of a tubular member.
Figure 11:
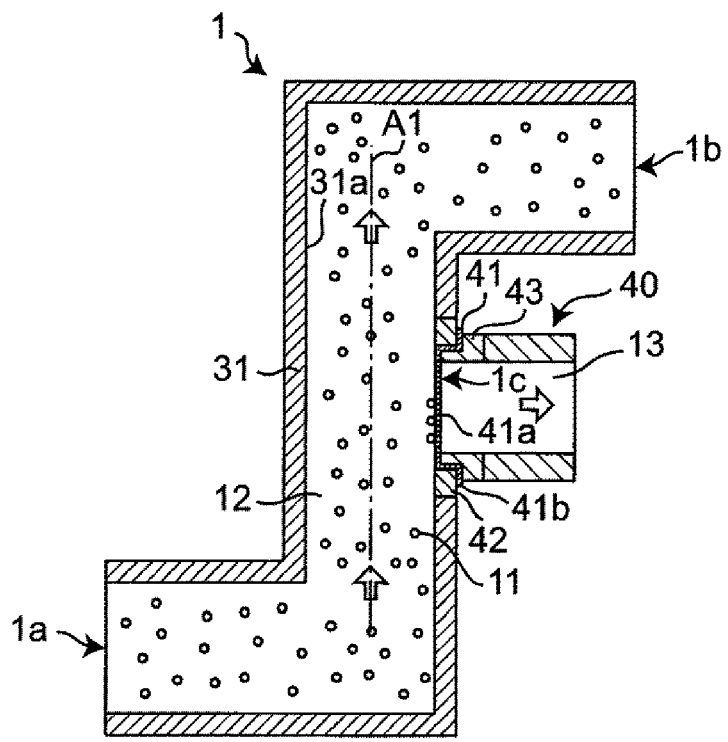
FIG. 11 is a cross-sectional view showing a modification of the tubular member.
Figure 12:
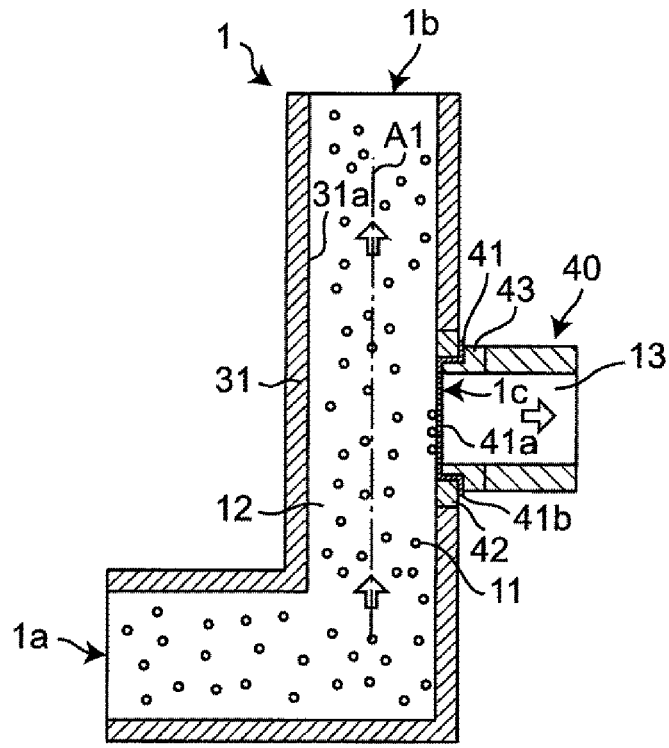
FIG. 12 is a cross-sectional view showing a modification of the tubular member.
Figure 13:
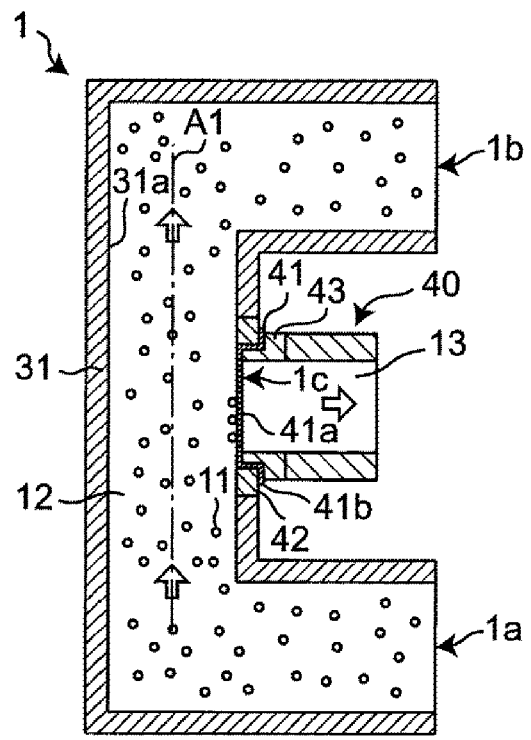
FIG. 13 is a cross-sectional view showing a modification of the tubular member.

In Embodiment 2, the first frame member 42b is formed in an L shape. In this case, it is substantially difficult to form the corner portion at a right angle, and the corner portion becomes an arc-shaped portion 42r as shown by a dotted line in FIG. 9. By coming into contact with the held portion 41d, the arc-shaped portion 42r may make it impossible to sufficiently reduce the distance d2 between the first frame member 42b and the second frame member 43 in the thickness direction D2 of the metallic porous membrane 41. Thus, the force with which the held portion 41d is held by the first frame member 42b and the second frame member 43 in the thickness direction D2 of the metallic porous membrane 41 will decrease. That is, the arc-shaped portion 42r may be a factor for decreasing the force with which the held portion 41d is held by the first frame member 42b and the second frame member 43 in the thickness direction D2 of the metallic porous membrane 41. Therefore, an annular groove 42c may be provided at the corner portion of the first frame member 42b so as to be recessed downward as shown in FIG. 9. By the groove 42c, it is possible to reduce the decrease in the force with which the held portion 41d is held by the first frame member 42b and the second frame member 43 in the thickness direction D2 of the metallic porous membrane 41. Each of the depth and the width of the groove 42c is, for example, 0.1 mm. In addition, similarly to the first frame member 42b, a groove may be provided at the corner portion of the second frame member 43.

Although the present invention has been fully described by way of preferred embodiments with reference to the accompanying drawings, various changes and modifications will be apparent to those skilled in the art. Therefore, unless such changes and modifications otherwise depart from the scope of the present invention as defined by the appended claims, they should be construed as being included therein.

Without limitation, the present invention is useful in the fields of chemical material purification, pharmaceutical production, and the like. Particularly, the present invention is useful for a filtration device that filters biological products contained in a liquid.

REFERENCE SIGNS LIST 1 filtration device
1a fluid introduction port
1b fluid discharge port
1c filtrate discharge port
2 fluid tank
3 pump
4 filtrate tank
11 filtration objects
12 fluid
13 filtrate
21, 22, 23, 24 pipe
31 tubular member
31a flow passage
40, 40A, 40B filtration filter
41 metallic porous membrane
41a membrane portion
41aa through hole
41b, 41c, 41d held portion
41ba, 41ca, 41da first bent portion
41bb, 41cb, 41db second bent portion
41dc third bent portion
41dd fourth bent portion
42, 42a, 42b first frame member
42aa bottom surface
42ab, 42ac contact surface
42ba third step portion
42c groove
42r arc-shaped portion
43 second frame member
43a, 43b first step portion
43c second step portion
43aa, 43ab contact surface
44 gap
PS1 first principal surface
PS2 second principal surface

The invention claimed is:

1. A filtration filter, comprising:
 (a) a metallic porous membrane having a center and including:
  (i) upper and lower opposed main surfaces;
  (ii) an inner membrane portion for filtering objects contained in a fluid, the inner membrane portion extending outwardly from the center of the metallic porous membrane and lying in a plane; and
  (iii) a held portion extending outwardly from an outer periphery of the inner membrane portion;
 (b) a lower frame having a first edge and a bottom surface, where the bottom surface of the lower frame does not extend below the lower main surface of the metallic Porous membrane; and
 (c) an upper frame having a second edge which is located radially inward of and below the first edge of the lower frame, the lower and upper frames cooperating to hold the held portion in such a manner that the held portion is bent around the first and second edges in a zig zag manner by the lower and upper frames themselves.

2. The filtration filter of claim 1, wherein the first edge is formed between first and second surfaces of the lower frame and the second edge is formed between first and second surfaces of the upper frame.

3. The filtration filter of claim 2, wherein:
 the first surfaces of the upper and lower frames lie parallel to the plane of the inner membrane portion;
 a portion of the upper surface of the metallic porous member extends along the first surface of the upper frame; and
 a portion of the lower surface of the metallic porous member extends along the first surface of the lower frame.

4. The filtration filter of claim 3, wherein the upper frame does not contact the lower surface of the metallic porous membrane.

5. The filtration filter of claim 2, wherein the first surface of the upper frame contacts the upper surface of the metallic porous member corresponding to a portion of the held portion but does not contact any portion of the upper surface of the metallic porous member corresponding to the inner membrane portion.

6. The filtration filter of claim 3, wherein the upper frame further includes a third surface extending parallel to its first surface, the second surface of the upper frame facing the second surface of the lower frame with a portion of the held portion extending there between, the third surface of the upper frame facing the first surface of the lower frame with a portion of the held portion extending there between.

7. The filtration filter of claim 6, wherein the distance between the second surface of the upper frame and the second surface of the lower frame as measured in a direction parallel to the plane of the inner membrane portion is greater than the distance between the third surface of the upper frame and the first surface of the lower frame as measured in a direction perpendicular to the plane of the inner membrane portion.

8. The filtration filter of claim 2, further including a gap formed between the second surface of the upper frame and the upper main surface of the porous membrane in an area between the first and second edges.

9. The filtration filter of claim 8, wherein:
 the first surfaces of the upper and lower frames lie parallel to the plane of the inner membrane portion;
 a portion of the upper surface of the metallic porous member extends along the first surface of the upper frame; and
 a portion of the lower surface of the metallic porous member extends along the first surface of the lower frame.

10. The filtration filter of claim 8, wherein the second surface of the upper frame extend perpendicular to the plane of the inner porous membrane.

11. A filtration filter, comprising:
 (a) a metallic porous membrane having a center and including:
  (i) upper and lower opposed main surfaces;
  (ii) an inner membrane portion for filtering objects contained in a fluid, the inner membrane portion extending outwardly from the center of the metallic porous membrane and lying in a plane; and
  (iii) a held portion extending outwardly from an outer periphery of the inner membrane portion;

(b), a lower frame having first and second edges; and (c) an upper frame having first and second edges, the first edge of the upper frame being located radially inward of and below the first edge of the lower frame, the second edge of the upper frame being located radially outwardly of and above the first edge of the lower frame, the second edge of the lower frame being located radially outward of and above the second edge of the upper frame, the lower and upper frames cooperating to hold the held portion in such a manner that the held portion is bent around the first and second edges of the upper frame and first and second edges of the lower frame in a zig zag manner by the upper and lower frames themselves.

12. The filtration filter of claim 11, wherein the first edge of the lower frame is formed between first and second surfaces of the lower frame and the first edge of the upper frame is formed between first and second surfaces of the upper frame.

13. The filtration filter of claim 12, wherein:
the first surfaces of the upper and lower frames lie parallel to the plane of the inner membrane portion;
a portion of the upper surface of the metallic porous member extends along the first surface of the upper frame; and
a portion of the lower surface of the metallic porous member extends along the first surface of the lower frame.

14. The filtration filter of claim 12, wherein the upper frame does not contact the lower surface of the metallic porous membrane.

15. The filtration filter of claim 12, wherein the first surface of the upper frame contacts a portion of the upper surface of the metallic porous member corresponding to a portion of the held portion but does not contact any portion of the upper surface of the metallic porous member corresponding to the inner membrane portion.

16. The filtration filter of claim 13, wherein the upper frame further includes a third surface extending parallel to its first surface, the second surface of the upper frame facing the second surface of the lower frame with a portion of the held portion extending there between, the third surface of the upper frame facing the first surface of the lower frame with a portion of the held portion extending there between.

17. The filtration filter of claim 16, wherein the distance between the second surface of the upper frame and the second surface of lower frame as measured in a direction parallel to the plane of the inner membrane portion is greater than the distance between the third surface of the upper frame and the first surface of the lower frame as measured in a direction perpendicular to the plane of the inner membrane portion.

18. The filtration filter of claim 12, further including a gap formed between the second surface of the upper frame and the upper main surface of the porous membrane in an area between the first and second edges.

19. The filtration filter of claim 18, wherein:
the first surfaces of the upper and lower frames lie parallel to the plane of the inner membrane portion;
a portion of the upper surface of the metallic porous member extends along the first surface of the upper frame; and
a portion of the lower surface of the metallic porous member extends along the first surface of the lower frame.

20. The filtration filter of claim 18, wherein the second surface of the upper frame extend perpendicular to the plane of the inner porous membrane.

\* \* \* \* \*